United States Patent
Levy

(10) Patent No.: US 6,512,012 B1
(45) Date of Patent: Jan. 28, 2003

(54) METHOD FOR THE CONTROL OF AQUATIC BREEDING INSECT POPULATIONS

(75) Inventor: Richard Levy, Fort Myers, FL (US)

(73) Assignee: Lee County Mosquito Control District, Lehigh Acres, FL (US)

( * ) Notice: Subject to any disclaimer, the term of this patent is extended or adjusted under 35 U.S.C. 154(b) by 0 days.

(21) Appl. No.: 09/484,740

(22) Filed: Jan. 18, 2000

Related U.S. Application Data

(60) Provisional application No. 60/116,873, filed on Jan. 22, 1999.

(51) Int. Cl.[7] ............................................... A01N 31/14
(52) U.S. Cl. ...................... 514/723; 514/722; 514/724; 514/738; 514/739; 424/405; 424/406
(58) Field of Search .................................. 424/405–409, 424/411, 417, 419–421; 514/722–724, 738, 739

(56) References Cited

U.S. PATENT DOCUMENTS

| | | | |
|---|---|---|---|
| 4,160,033 A | | 7/1979 | Garrett et al. ............... 424/285 |
| 4,707,359 A | | 11/1987 | McMullen .................... 424/92 |
| 4,818,534 A | * | 4/1989 | Levy ........................... 424/404 |
| 5,439,683 A | * | 8/1995 | Hodakowski ............... 424/408 |
| 5,635,194 A | | 6/1997 | Dorn et al. .................. 424/405 |

FOREIGN PATENT DOCUMENTS

| | | |
|---|---|---|
| DE | 1357952 | 6/1974 |
| DE | 1557804 | 12/1979 |

OTHER PUBLICATIONS

Dorn et al Abstract HCAPLUS # 1997:700918 Ecotoxicology 6(5) pp 275–292 '97.*
Lesyuk et al Abstract HCAPLUS # 1987:1408 Eksp. Vodn. Tokiskol. 9, 56–67 '84.*
Tomah Products Inc. Publication: "Tomadol™ Alcohol Ethoxylates, Safety and Biodegradability." Nov. 5, 1999.
Shell Chemical Company Publication: "Storage and Handling of NEODOL® Alcohols and Ethoxylates"; Copyright 1997.
Tomah Products Inc. Publication: "Tomadol™ a new name in alcohol ethoxylates." Jul. 19, 1999.
Synapse Information Resources: Handbook of Industrial Surfactants—Third Edition, vol. 1; Compiled by Michael and Irene Ash: 2000.
Synapse Information Resources: Handbook of Industrial Surfactants—Third Edition, vol. 2; Compiled by Michael and Irene Ash: 2000.
Tomah Products Inc. Material Data Sheet for TOMADOL 1–3: Prepared Jun. 30, 1999.
Tomah Products Inc. Material Data Sheet for TOMADOL 91–2.5: Prepared Jul. 29, 1999.

* cited by examiner

Primary Examiner—Neil S. Levy
(74) Attorney, Agent, or Firm—Mark A. Litman & Assoc. P.A.

(57) ABSTRACT

The application of film-forming compositions to aquatic sites, especially aquatic breeding sites for control of surface-active aquatic breeding insects other than black flies, especially for immature mosquitos, has been found to be enhanced when different compounds than those suggested in the prior art are used. The compounds according to the present invention comprise film-forming chemicals which are biodegradable, nonionic, insoluble or partially soluble in water, and include $C_6$, $C_7$, $C_8$, $C_9$, $C_{10}$, and $C_{11}$ alcohol ethoxylates, propoxylates, and/or alkoxylates with an average of one (1) to five (5) moles of ethylene and/or propylene oxide per mole of alcohol, and mixtures thereof. The compositions may be applied directly as liquids or released into the aquatic environment from a carrier, such as a biodegradable, water-erodible, water-soluble or water-dispersible carrier. Compositions may also be formulated with chemical or microbial pesticides prior to application as a liquid or from a carrier for enhanced single stage or multistage insect control.

11 Claims, No Drawings

METHOD FOR THE CONTROL OF AQUATIC BREEDING INSECT POPULATIONS

This application claims the benefit of Provisional Application No. 60/116,873 filed Jan. 22, 1999.

BACKGROUND OF THE INVENTION

1. Field of the Invention

This invention relates to insecticide compositions and methods for controlling the breeding of insects which have aquatic breeding sites.

2. Background of the Art

In the specification of our British Pat. Nos. 1 357 952 (March 1971) and 1 557 804 (October 1976) there is disclosed a method of controlling the breeding of mosquitoes by forming an insoluble monomolecular layer on the surface of water to reduce the number of mosquito pupae and larvae.

The monomolecular layer is particularly effective in killing the mosquito at certain stages of the life cycle, namely the ovipositing female, fourth stage larva, pupa and emerging adult. It is lethal because the decrease in surface tension causes wetting of the respiratory trumpets of the pupae and larvae and also forms a physical barrier to surface penetration, thus preventing oxygen uptake from the atmosphere by the larvae and pupae. The application of monolayers to the control of mosquito juveniles is described in:

1. McMullen, A. I. & Hill, M. N., (1971), Nature, 234, No. 5323 pp 51–52.
2. McMullen, A. I., Reiter, P. & Phillips, M. C., (1977), Nature, 267, No. 5608 pp 244–245.
3. Garrett, W. D., (1976), Naval Res. Lab. Report 8020, p 13, Washington D.C.

In the specification of our British Pat. No. 1 561 088 there is disclosed a method of controlling the breeding of insects which have an aquatic phase in their life cycle by forming an insoluble foam layer on the surface of the water. This foam layer presents an impenetrable barrier to pupae and larvae of the insects, again wetting their respiratory system and preventing oxygen uptake.

The foam method is more effective than the monomolecular method in that it is effective in killing the mosquito at all stages in its life cycle, namely: ovipositing female, egg, first, second, third and fourth stage larva, pupa and emerging adult. It is, however, more expensive than the monomolecular method in both dosage and application equipment.

There are also specific toxins obtained from *Bacillus thuringiensis* cultures (hereinafter referred to as B.t.) and from *Bacillus sphaericus* cultures which are mainly effective against first, second and third stage mosquito larvae but suffer from the disadvantage that the toxin crystal is dense and rapidly sinks below the feeding zones of young larvae. It is also rapidly inactivated by particulate matter in the catchment.

U.S. Pat. No. 4,707,359 describes an insecticide composition for controlling the breeding of insects (particularly mosquitos) which have aquatic breeding sites comprises two components, the first being either an insoluble monomolecular layer, an insoluble foam layer or a duplex film layer and the second having a toxic action on larvae, the combination of the two components providing a synergistic mixture. In particular, this patent describes an insecticide composition for controlling insects which have an aquatic breeding site, comprising an effective insecticidal amount of a first component which when applied to the surface of a water catchment forms an insoluble monomolecular layer or an insoluble foam layer effective in killing insects at certain stages in their life cycle, said first component being selected from the group consisting of:

a) $C_mH_{2m+1}.(OR)_{mn}OH$, b) $C_mH_{2m}-1.(OR)_nOH$, c) $C_mH_{2m}+1.(OR.OB)_nOH$, d) $C_mH_{2m-1}(OR.OB)_nOH$, e) $C_mH_{2m+1}.CO.(OR)_nOH$, f) $C_mH_{2m-1}.CO.(OR)_nOH$, g) $C_mH_{m2m+1}.CO.(OR.OB_nOH$, and h) $C_mH_{m2m-1}.CO.(OR.OB)_nOH$, where R and B are alkylenes and may be the same or different, n is an integer in the range 1 to 3 and m is an integer greater than 14, said group being exclusive of isostearyl ethoxylates; and an effective larvicidal amount of a second component comprising a mosquito larva toxin obtained during growth of bacterial cultures, the first and second components giving rise to a synergistic mixture having a greater effectiveness in control of insects than that exhibited by either the first or second component alone.

There is provided an insecticide composition for controlling insects which have an aquatic breeding site comprising a first component which is capable of forming either a monomolecular layer, an insoluble foam layer or a duplex film layer on the surface of a water catchment and a second component which has a toxin action (preferably rapid) on larvae, giving rise to a synergistic mixture. The first component may be any one or more of the compounds referred to in the specification of British Pat. Nos. 1 557 804 and 1 561 088. Thus the first component may include at least one long chain compound of the general formula:

$$CmH2m+/-1.(OR)nOH$$

or $$CmH2m+/-1.(OR.OB)nOH$$

and/or at least one long chain compound of the general formula:

$$CmH2m+/-1.CO.(OR)nOH \text{ or } CmH2m+/-1.CO.(OR.OB)nOH$$

where these include branched chain isomers, but excepting isostearyl alcohol or acid.

It was asserted to be unexpected that by mixing the toxin from *Bacillus thuringiensis* or *Bacillus sphaericus* with the material forming the monomolecular layer, the toxin was retained at the surface for quite long periods and was transported or spread over wide areas. When the toxin was mixed with an insoluble foam layer the toxin is held at the surface for periods depending on the speed of breakdown of the foam, which depends on the amount applied and the extent of water pollution. Alternatively, the monomolecular layer and toxin mixture were applied to the water surface with a thin oil layer applied on top thereof, thus forming a "duplex film". These methods of applying the toxin to a water catchment resulted in a much more effective method for killing mosquitoes than by applying the monolayer, foam, thin oil or the toxin alone. Thus the combination produced a synergistic mixed product. In these formulae, R and B are alkylenes and may be the same or different, n is an integer in the range 1 to 3 and m is an integer greater than 14. The second component may be any specific mosquito larval toxin such as that obtained during growth of bacterial cultures, for example, that toxin found in *B. thuringiensis* H-14 (Bt-H14) or in *B. sphaericus* preparations, the toxin being a high molecular weight protein which splits into active sub-units inside the larvae.

U.S. Pat. No. 4,160,033 describes the use of a nonionic, autophobic, organic material with a density less than that of water, a boiling point of 170 degrees Centigrade or more, a freezing point of less than 5 degrees Centigrade, an HLB number of 10 or less, a bulk viscosity of less than 1000 Centistokes at the temperature of use, a spreading velocity of 10 cm/sec for the first 100 cm, and a surface tension effectiveness which lowers the surface tension of said body of water to 30 dynes/cm or less. The specifically disclosed materials for use within this process are described as sorbitan monooleate, a solution of 70 volume percent to less than 100 volume percent of sorbitan monooleate and 2-ethylbutanol; saturated, branched chain alcohols with a total carbon content of from 15 to 19 carbon atoms and one to three oxyethylene groups; unsaturated cis alcohols with 15 to 19 carbon atoms in the chain length; unsaturated ethers with a chain length of 12 to 18 carbon atoms and three to five oxyethylene groups; and oleyl ether with two oxyethylene groups, and combinations of these compounds. The preferred materials for use alone or in combination include sorbitan monooleate, isostearyl alcohol, lauryl ether, and oleyl ether. Such a compound or combination of compounds is capable of forming an insoluble monomolecular layer, a foam layer or, (in the presence of an oil), a duplex film, on the surface of a water catchment.

U.S. Pat. No. 5,635,194 describes the use of water-soluble, detergent-range, ethoxylated alcohols to control black fly larvae in aquatic habitats. The mechanism of larvicidal activity described in the patent relates only to persistent subsurface targeting of black fly larvae that are attached to various submerged substrates and does not describe or contemplate any activity against any aquatic species at the air-water interface. The reference is specifically silent as to effects upon immature mosquitoes at the air/water interface of aquatic habitats.

SUMMARY OF THE INVENTION

The application of film-forming compositions to aquatic sites, especially aquatic breeding sites for surface-active, aquatic breeding insects, especially for mosquito larvae and mosquito pupae, has been found to be enhanced when different compounds than those suggested in the prior art are used. The compounds according to the present invention comprise film-forming chemicals which are biodegradable, nonionic, insoluble or partially soluble in water, and include $C_6$, $C_7$, $C_8$, $C_9$, $C_{10}$, and $C_{11}$, alcohol ethoxylates, propoxylates, and/or alkoxylates with an average of one (1) to five (5) moles of ethylene and/or propylene oxide per mole of alcohol, and mixtures thereof. Examples of commercial materials of interest include, for example, Neodol® 91-2.5 which is a mixture of $C_9$–$C_{11}$ alcohol ethoxylates with average of 2.5 moles of ethylene oxide per mole of alcohol, Neodol® 1-3 and Neodol® 1-5 which are $C_{11}$ alcohol ethoxylates with 3 and 5 moles of ethylene oxide per mole of alcohol, respectively, Alfonic® 610-3.5 Ethoxylate and Alfonic® 810-2 Ethoxylate which are $C_6$–$C_{10}$ and $C_8$–$C_{10}$ alcohol ethoxylate mixtures containing 3.5 and 2 moles of ethylene oxide per mole of alcohol, respectively, and Iconol®E DA-4 which is a $C_{10}$ 4-mole ethylene oxide adduct of decyl alcohol. These film-forming materials, which have shorter carbon chains than the film-forming materials described for use by the prior art show improved results in comparison with some of the longer carbon chain length compounds of the prior art.

The components of the insecticide application may be formulated for application to water in several ways. These methods include:

(1) Approximately Monomolecular Layer or Multimolecular Layer Application,
(2) Substantive or Transient Foam Application
(3) Delayed Release Application for Formation of Approximately Monomolecular Layer or Multimolecular Layers
(4) Spray Application, or
(5) Combined Application With Insecticidal Materials (e.g., as in U.S. Pat. No. 4,707,359).

Method (1) may be effected, for example, where the first component is in the form of a hydrophobic soft wax or "oil" at ambient temperatures and is applied directly to the water surface.

Method (2) may be effected, for example, when the first component may be solid or semi-solid, it may be prepared by gradually adding it to water being stirred vigorously in a high speed mixer, emulsifier or colloid mill to form a dispersion having a concentration of from 10% to 20% w/v. A substantive foaming agent, such as a thickener, surfactant, detergent, foaming agent or the like may be combined with the film-forming compositions of the present invention for application to water. Additional film-forming materials of the prior art may be blended with the film-forming materials of the present invention. However, the film-forming materials of the present invention should comprise at least 10%, at least 20%, at least 30%, at least 40%, at least 50%, at least 60%, at least 70%, at least 80%, at least 90%, at lest 95% or even 100% by weight or volume of all organic and/or inorganic film-forming materials used in the applied compositions. The higher the proportion of the film-forming compounds of the present invention, apparently the higher the insecticidal efficacy of the compositions used, even without any toxicological insecticidal agents used. Foam formulations may also be produced most easily from monomolecular layer formulation (B) described above (but, for example, diluted with water to 1% of the active ingredient) by the injection of air, in situ generation of foam with foaming agents, or other gases using foaming equipment as described in British Pat. No. 1 561 088. It is preferable that the foam layer formed is at least 0.1 cm in thickness. The foam may be applied at a rate of 1.0 to 5.0 g of active ingredient per square meter which forms a foam layer about 0.1 to 0.5 cm in thickness and which may reduce to a single bubble layer eventually or monomolecular layer or multimolecular layer, which is still effective.

The applied insecticide composition may include an extender (either water-soluble, water-dispersible, or water-insoluble) such as water or an oil, for example a vegetable oil such as soya bean oil or coconut oil or a light mineral oil such as diesel oil, petrol oil, diesel oil, etc., but these tend to contribute undesirable contaminants to the aquatic environment and are not preferred. Dyes may be used with the composition to assist in the visibility of the application, preferably water-soluble or oil-soluble dyes, more preferably dyes which decompose or are bleached by extended exposure to air, natural light, and/or water.

The insecticide composition once formulated may be applied to water to form a monomolecular layer, a multimolecular layer (or two, three or more layers, or a layer hydrophilically or hydrophobically or coupled continuous or discontinuous layer) associated with the surface as a self-spreading suspension of "slurry" by means of droppers, drip-feed reservoirs, spray equipment or by sorbent and inert materials (e.g., which may be preferably biodegradable, soluble or insoluble) which have been soaked in the concentrated mixture and which float on the surface of the water or which sink in the water and quickly or slowly (as desired) releases the composition.

When the surface of the water or aquatic area to be treated is moving water, the surface must be made static by employing a physical barrier, e.g., by means of a buoyant boom tethered or anchored around the appropriate area. Suitable physical barriers are described in British Patent Specification No. 1 561 088. The preferred compositions according to the present invention contain no unspecific toxin or pollutive materials, and the materials used are biodegradable. However, pesticides such as insecticides, larvicides, pupicides, herbicides (the destruction of which can also assist in the reduction in pests by removing material essential to their habitat) and the like may be used where additional active effects are found to be necessary.

DETAILED DESCRIPTION OF THE INVENTION

Surface-film technology has been shown to be applicable to mosquito control. Nonionic organic monomolecular or duplex films have been shown to be effective against the immature stages of most species of mosquitoes in a variety of water or aquatic environments. Laboratory and field evaluations have mainly focused on the control of larvae and pupae; however, some studies have shown the potential for controlling floating eggs/egg rafts and emerging adults or ovipositing females.

Unlike the central nervous system, endocrine system, and stomach or contact poison effects of larvicidal products such as organophosphates, phenyl-pyrazoles, growth regulators, and bacteria, the mode of action of these biodegradable surface-active films is nontoxic via a physicochemical mechanism that reduces the surface tension of the aquatic mosquito habitat causing a wetting of the tracheal structures (e.g., larval siphon or pupal trumpets) which assists in and/or causes the subsequent drowning of larvae and pupae. Since death is induced by a physical effect of the surface film at the air-water interface, resistance of mosquito populations to these types of chemicals is not expected to develop. This is a significant improvement over the use of pesticidal materials since the ability of insects to develop resistance to specific pesticides has been well documented and reported in the literature.

Although surface films have been proven to be effective in controlling mosquito larvae, the speed of action is usually slow. Larval instar, species, habitat, oxygen levels, wind speed and direction, runoff, tidal fluxes, emergent and floating vegetation, and surface debris have been shown to have a dramatic effect on the mosquito-controlling efficacy of surface films. Therefore, a surface film, mixture of surface films, or surface film formulation having a faster physical mode of action on larval mosquito populations at the air-water interface or providing more consistent delayed efficacy would help compensate for the adverse or inhibitory effects caused by the aforementioned habitat and environmental/climatological fluctuations.

Product Classification: Film-forming chemicals of the present invention are biodegradable nonionic, insoluble or partially soluble in water, and include $C_6$, $C_7$, $C_8$, $C_9$, $C_{10}$, and $C_{11}$ alcohol ethoxylates, propoxylates, and/or alkoxylates with an average of one (1) to five (5) moles of ethylene and/or propylene oxide per mole of alcohol, and mixtures thereof. Examples of products of interest are Neodol® 91-2.5 which is a mixture of $C_9$–$C_{11}$ alcohol ethoxylates with average of 2.5 moles of ethylene oxide per mole of alcohol, Neodol® 1-3 and Neodol® 1-5 which are $C_{11}$ alcohol ethoxylates with 3 and 5 moles of ethylene oxide per mole of alcohol, respectively, Alfonic® 610-3.5 Ethoxylate and Alfonic® 810-2 Ethoxylate which are $C_6$–$C_{10}$ and $C_8$–$C_{11}$ alcohol ethoxylate mixtures containing 3.5 and 2 moles of ethylene oxide per mole of alcohol, respectively, and Iconol® DA-4 which is a $C_{10}$ 4-mole ethylene oxide adduct of decyl alcohol.

Film-forming product examples of interest have the following Hydrophile-Lipophile Balance No., Pour Point (° C.), and Specific Gravity (77/77° F.) parameters, respectively. Neodol® 91-2.5 parameters are 8.5, −13, and 0.925; Neodol® 1-3 parameters are 8.7, −7, and 0.936; Neodol® 1-5 parameters are 11.2, 6, and 0.966; Alfonic® 610-3.5 Ethoxylate parameters are 10.0, −7, and 0.95; Alfonic® 810-2 Ethoxylate parameters are 8.0, −15, and 0.92; and Iconol® DA-4 parameters are 11.0, −24, and 0.958.

Film-forming chemicals of the present invention can also be mixed with solvents such as water soluble alcohols (e.g., ethanol, methanol, or 2-propanol, etc.) to enhance, activate or synergize the film-forming chemicals; however, these solvents generally show poor efficacy against immature mosquitoes when used alone.

Product Uses: Film-forming chemicals of the present invention can be used as a partially active formulation ingredient with any chemical or microbial mosquito larvicide or pupicide (e.g., pirimiphos-methyl, lambda-cyhalothrin, temephos, chlorpyrifos, methoprene, pyriproxyfen, diflubenzuron, phenyl-pyrazole, *Bacillus thuringiensis* var. *israelensis, Bacillus sphaericus, Spinosyns, Lagenidium giganteum*, polyoxyethylene (2) isostearyl alcohol, petroleum oils, etc.) to rapidly produce multistage control (e.g., rapid larval and pupal kill) by enhancing or synergizing the action of the chemical or microbial insecticide as well as improving water-surface coverage and vegetative penetration of the product(s) mixed with the film-forming chemicals. Film-forming chemicals of the present invention can be used as a technical active ingredient for killing mosquito larvae and pupae at the air-water interface, to sink or inhibit the eclosion of floating eggs or egg rafts, and to entrap and drown ovipositing females, resting males, and emerging adults. Pupae of certain mosquito species can be significantly more sensitive to surface films than larvae. Film-forming chemicals of the present invention can also be used to control the surface-active aquatic stages of certain non-mosquito invertebrate pests such as nuisance aquatic insects (e.g., midges, sand flies). The use of these film-forming chemicals in fish farming or aquaculture to control predacious insects is also proposed.

The activity of the compounds and compositions of the present invention is effective against surface-active aquatic species during their surface-active stage. The surface active stage is when the aquatic species lives at or near the surface of the aquatic habitat or passes through the air-aquatic habitat interface, or breeds and breaths within or near the air-aquatic habitat interface.

Product Formulation. Film-forming chemicals of the present invention can be used alone as a neat formulation or can be mixed neat or with water, water soluble alcohols, surface active chemicals, oils or conventional mosquito larvicides. The formulation of choice for each film-forming chemical, mixture or formulation will be dependent on the physicochemical characteristics of the film-forming chemical or chemicals utilized to control the target pest(s). Film-forming chemicals or formulations can also be formulated into solid compositions that have a specific gravity less than, equal to, or greater than 1.0 (e.g., granules, pellets, or briquets). Soluble or insoluble, biodegradable or erodable carriers (which are preferred) for the film-forming compositions of the present invention may be non-superabsorbent polymers, natural products (e.g., papers, cellulosic solids, water-insoluble porous materials which absorb or adsorb the film-forming material within the structure, water-soluble porous materials which absorb or adsorb the film-forming material within the structure, porous containers which merely slowly release a volume of the film-forming material, porous containers which both dissolve and physically release volumes of the film-forming composition through pores, and the like. In general, selection of an effective application rate can depend on habitat depth, surface debris, emergent and surface vegetation, organic matter, microbial and algal concentration, the specific target species, and the developmental stage of the target species.

Product Application Rates: Film-forming chemicals of the present invention can be applied by ground or aerial techniques as technical, water-base, solvent-base, oil-base or solid formulations as well as admixtures with pesticides or pesticide formulations at application rates of ca. 0.3–2.0 gallons of film-forming chemical(s)/surface acre of water.

These and other non-limiting aspects of the present invention will be supported at least in part by the following examples.

EXAMPLE 1

Comparative bioassays with the film-forming chemicals Neodol® 91-2.5 and Agnique® MMF were conducted against ten 1st, 2nd, 3rd, or 4th instar larvae or a mixed population of five 3rd or 4th instar larvae and five pupae of Aedes, Anopheles, or Culex species in glass crystallizing dishes (65×125 mm) containing 500 ml of fresh (water purified by reverse osmosis filtration) or brackish water (distilled water/Instant Ocean®). Film-forming chemicals were applied to the surface of the water with a hypodermic syringe. Larvae were fed ground rabbit chow or liver powder throughout a test. Tests were replicated three times. Bioassays were conducted in a room maintained at ca. 26–27° C. Bioassay results are summarized in Table 1.

Test against 1st–4th Aedes, Anopheles or Culex indicated that Neodol® 91-2.5 provided significantly faster and more reliable mosquito-controlling efficacy when compared to Agnique® MMF. Agnique® MMF is registered by the Environmental Protection Agency as a mosquito larvicide and pupicide and is the current industry standard for a product classified as a monomolecular surface film. Agnique® MMF is a $C_{18}$ alcohol ethoxylate with an average of 2 moles of ethylene oxide per mole of alcohol while Neodol® 91-2.5 is a $C_9/C_{10}/C_{11}$ alcohol ethoxylate mixture with an average of 2.5 moles of ethylene oxide per mole of alcohol. These tests suggest the relationship between carbon chain length and larvicidal efficacy.

EXAMPLE 2

A mixture of Abate® 4-E and Neodol® 91-2.5 was added to water in a concentration to produce an aqueous formulation containing 0.5 or 1 fl. oz. Abate® 4-E/acre and 0.3, 0.4, or 0.5 gal/Neodol® 91-2.5/acre when applied as a 5.0 gal/acre water-based suspension. Film-forming chemicals were applied to the surface of the water with a hypodermic syringe. Bioassays with these formulations against mixed populations of five 3rd or 4th instar larvae and five pupae of Ae. aegypti, Ae. taeniarhynchus, or Cx. quinquefasciatus produced 100% control within 24 hrs with all formulations. Similar rapid multistage control was also observed within 24 hr posttreatment when tests were conducted against larvae and pupae with formulations of Bacillus thuringiensis var. israelensis (Vectobac®) and Neodol® 91-2.5.

EXAMPLE 3

The relationship between Neodol® 91-2.5 application rate and mosquito-controlling efficacy was evaluated in a series of bioassays (Table 2). Comparative bioassays were conducted against Aedes, Culex and Anopheles spp. larvae in 400 ml or 800 ml glass beakers or crystallizing dishes containing 250 or 500 ml of fresh or brackish water at application rates of ca. 0.5 to 0.7 gal film-forming chemical/ surface acre of water. Film-forming chemicals were applied with a hypodermic syringe. Results indicated that application rates of 0.5 and 0.62 were not generally effective in controlling the mosquito populations while a rate of ca. 0.7 gal/acre provided 100% control of all instars and species of mosquitoes evaluated.

EXAMPLE 4

Comparative bioassays against Aedes, Anopheles, and Culex spp. larvae were conducted in 400 ml glass beakers containing 250 ml of fresh or brackish water with technical Neodol® 91-2.5 and solvent admixtures of Neodol® 91-2.5 (Table 3). Solvents utilized in the admixtures were technical methanol, ethanol, and 2-propanol at rates of 25 or 50% (w/w) solvent. Application rates (i.e., total and Neodol® active ingredients) varied with the type of formulation (i.e., solvent versus technical). Film-forming chemicals/ formulations were applied to the water surface with a hypodermic syringe (3 replications/formulation).

Results of bioassays suggested that technical Neodol® and some solvent formulations of Neodol® can be effective in controlling mosquito larvae. It was interesting to note that the bioassays in Table 2 indicated that Neodol® 91-2.5 application rates of ca. 0.5–0.6 gal/acre were generally ineffective in consistently controlling mosquito larvae. However, solvent formulations containing from ca. 0.3–0.5 gal/acre of technical Neodol® 91-2.5 were shown to provide excellent control of all instars of the mosquito larvae. In some cases, solvent formulations performed better than the technical product at lower rates. No efficacy against mosquito larvae was observed when the technical solvents were applied at ca. 0.71 gal/acre. The increased efficacy was presumed to be due to a solvent-induced synergism or activation of the Neodol® 91-2.5 that produced improved or rapid wetting of the tracheal system of the larvae causing anoxia and drowning.

EXAMPLE 5

Comparative bioassays (see Example 4, Table 3) against 4th instar larvae of Anopheles quadrimaculatus in brackish water at 3.0 gal/acre with aqueous (water purified by reverse osmosis filtration) formulations of technical Neodol® 91-2.5 and aqueous 75%/25% formulations or Neodol® 91-2.5/methanol, ethanol, or 2-propanol produced 100% mortality within 24 hr posttreatment. Similar results (i.e., 100% control) were obtained in tests against 4th instar larvae of Culex quinquefasciatus with a 3.0 gal/acre application rate of aqueous formulations of Neodol® 91-2.5/ methanol or 2-propanol. However, only 16.7% mortality of larvae was obtained with an aqueous formulation of technical Neodol® 91-2.5 in the same 24 hr test period.

In general, initial results suggested that water can be a useful diluent for applying technical or solvent-enhanced formulations of Neodol® 91-2.5 for control of mosquito larvae.

EXAMPLE 6

Neodol® 91-2.5 was also evaluated against immature stages of Aedes, Anopheles, or Culex species in 33.0×22.9×

5.1 cm glass pans (0.0993 m² water surface) containing 1000 ml (1.9 cm depth) or 2000 ml (3.8 cm depth) of fresh (water purified by reverse osmosis filtration) or brackish (10% seawater—distilled water/Instant Ocean®) water and ten 1st to 4th instar larvae and/or pupae (Table 4).

A glass pipette (0.1 ml) was used to deliver the Neodol® 91-2.5 to the water surface of each pan (3 replications/trial). Larvae were fed ground rabbit chow or liver powder throughout a test. Bioassays were conducted in a room maintained at ca. 26–27° C.

In general, results of bioassays suggested that water volume and/or depth could have an impact on the larvicidal effectiveness of Neodol® 91-2.5. Several tests conducted in 2000 ml of water at a depth of 3.8 cm did not produce 100% control of larvae in 1 day; however, 100% control of larvae was observed within 2 to 6 days posttreatment. Slower pupicidal efficacy was also recorded in tests in 2000 ml of water.

EXAMPLE 7

Acute 24 or 48 hr comparative bioassays were conducted against *Culex quinquefasciatus* larvae with Neodol® 91-2.5 or a Neodol® 91-2.5/methanol formulation in 5 gal plastic buckets (0.06379m² water surface) containing 1920, 7580, or 16,880 ml of fresh water (water purified by reverse osmosis filtration) and 10 larvae. Water depths at the volumes indicated were 5.1, 15.2, or 30.5 cm, respectively (Table 5). Neodol® formulations were applied to the water surface with a glass (0.1 ml) pipette. Tests were replicated three times. Larvae were fed ground rabbit chow throughout a test. Tests were conducted at 26–27° C.

Results of these bioassays indicated that water volume and depth can have a significant effect on the control of larvae with Neodol® 91-2.5. The data showed that the rate of control decreased as the volume and depth increased. However, the delayed effect was overcome in one test using a solvent mixture of Neodol® 91-2.5.

EXAMPLE 8

The mosquito-controlling efficacy of several Neodol® ethoxylated alcohol film-forming agents and mixtures having carbon chains of $C_9/C_{10}/C_{11}$ (Neodol®) 91-2.5), $C_{11}$ (Neodol® 1-3), $C_{12}/C_{13}$ (Neodol® 23-1), and/or $C_{12}/C_{13}/C_{14}/C_{15}$ (Neodol® 25-3) was evaluated against larvae of Aedes, Anopheles, and Culex species in a series of 1 or 2-day shallow-water bioassays at application rates of 0.3, 0.5, or 0.7 gal/acre (Table 6). Bioassays were conducted in glass pans (33.0×22.9×5.1 cm) containing 2000 ml (3.8 cm depth) of fresh water (water purified by reverse osmosis filtration) and 10 larvae (3 replications/test). Neodol® film-forming agents/formulations were applied to the water surface with a glass pipette (0.1 ml). Larvae were fed ground rabbit chow or liver powder throughout a test. Tests were conducted in a room maintained at 26–27° C.

Bioassays indicated that $C_{11}$ or $C_9/C_{10}/C_{11}$ alcohol ethoxylates or mixtures of these products were significantly more effective as acute larvicides when compared to $C_{12}/C_{13}$ or $C_{12}/C_{13}/C_{14}/C_{15}$ alcohol ethoxylates. It should be noted that the $C_9/C_{10}/C_{11}$ alcohol ethoxylate was also significantly more effective against mosquito larvae than the $C_{18}$ alcohol ethoxylate (Agnique® MMF) in another series of comparative bioassays (see Table 1). Bioassays further indicated that application rate was important and that Neodol® 1-3 could provide 100% control of larvae within 24 hr posttreatment at 0.7 gal/acre; however, a mixture of Neodol® 91-2.5 and Neodol® 1-3 showed enhanced larvicidal action over Neodol® 1-3 alone at 0.3 and 0.5 gal/acre.

EXAMPLE 9

The acute or chronic larvicidal efficacy of $C_9/C_{10}/C_{11}$ (Neodol® 91-2.5), $C_{11}$ (Neodol® 1-3), $C_{12}/C_{13}$ (Neodol® 23-1 or Neodol® 23-3), or $C_{12}/C_{13}/C_{14}/C_{15}$ (Neodol® 25-3) alcohol ethoxylates or mixtures was evaluated against Anopheles and Culex larvae in a series of deep-water bioassays conducted at 0.7 gal/acre (Table 7). Bioassays were conducted in plastic 5 gal buckets containing 10 larvae and 16,880 ml (30.5 cm depth) of fresh water (3 replications/test). Larvae were fed ground rabbit chow or liver powder throughout a test. Bioassays were conducted in a room maintained at 26–27° C.

Results of bioassays indicated that Neodol® 91-2.5, Neodol® 1-3, or a mixture of Neodol® 91-2.5 and Neodol(® 1-3 could provide effective acute or delayed larvicidal action. However, several comparative tests with Neodol(® 23-1, Neodol(® 23-3, or Neodol® 25-3 resulted in significantly lower levels of control within 24 hr posttreatment and/or ineffective delayed control at 6 days posttreatment. Mixtures of Neodol® 91-2.5 and Neodol® 23-1, 23-3, or 25-3 were significantly less effective than a mixture of Neodol® 91-2.5 and Neodol® 1-3. This data and data in Example 8 suggested the importance of carbon chain length in larvicidal efficacy and indicated that ethoxylated alcohols or blends containing $C_{12}$ or greater carbon chains are significantly less effective against mosquito larvae when compared to ethoxylated alcohols and mixtures of $C_{11}$ or less.

EXAMPLE 10

The efficacy of surface films of Neodol® 91-2.5 and a mixture of Neodol® 91-2.5 and Neodol® 1-3 as an adult male and female entrapment aid and oviposition inhibitor was evaluated against *Culex quinquefasciatus* in a series of bioassays (Table 8). One glass crystallizing dish (65×125 mm) containing 500 ml of fresh water was placed in the center of a 30.5×30.5×30.5 cm cage containing ca. 100 or 250 adult mosquitoes. Surface films were applied to the water surface at a rate of 0.7 gal/acre. Control cages contained surface film-free water. Tests were replicated 3 times.

Adult mosquitoes in each cage were fed sugar water and blood fed prior to the introduction of the crystallizing dishes. The number of adult males and females entrapped on the surface of the water, and the number of egg rafts laid in test and control cages were compared to the two surface film types.

Results indicated that Culex males alighting on the surface of the water to drink or rest and female mosquitoes alighting on the surface to drink, rest, and/or oviposit can be entrapped and drowned by the reduced surface tension produced by the Neodol® products. The data also showed that significantly fewer eggs were laid on water surfaces treated with the Neodol(V alcohol ethoxylates when compared to water surfaces containing no Neodol® products. Observations also indicated that fewer larvae hatched from egg rafts on water surfaces treated with Neodol® alcohols when compared to controls. This suggested the potential ovicidal or eclosion-inhibiting characteristics of $C_{11}$ or $C_9$–$C_{11}$ alcohol ethoxylates.

EXAMPLE 11

Additional shallow-water acute bioassays with a variety of technical film-forming agents (Neodol(® 91-2.5, Neodol® 1-3, Neodol(® 23-1 or Agnique® MMF) or mixtures of film-forming agents (Neodol® 91-2.5/Neodol(® 1-3, Neodol® 91-2.5/Iconol® DA-4, Neodol® 1-3/ Neodol® 1-5, and Neodol® 91-2.5/Neodol® 1-5 were conducted against Aedes or Culex larvae to further evaluate the comparative mosquito-controlling efficacy between $C_9$–$C_{11}$ and $C_{12}$–$C_{18}$ ethoxylated alcohols (Table 9). Bioassays were conducted in glass pans (33.0×22.9×5.1 cm) containing 2000 ml (3.8 cm depth) of fresh water (water purified by reverse osmosis filtration) and 10 larvae (3 replications/film-forming agent(s). Film-forming agents or mixtures were applied to the water surface with a glass pipette (0.1 ml). Larvae were fed ground rabbit chow throughout a test. Tests were conducted in a room maintained at 26–27° C.

In general, results at application rates of 0.7 gal/acre indicated that several $C_9$–$C_{11}$ or $C_{11}$ alcohol ethoxylate film-forming agents or mixtures were significantly better than $C_{12}$–$C_{13}$ or $C_{18}$ alcohol ethoxylates in providing acute mortality of larvae within 24 hr posttreatment.

EXAMPLE 12

Water-base or solvent (i.e., methanol) mixtures of $C_6$–$C_{11}$ alcohol ethoxylate film-forming chemicals (i.e., Neodol® 91-2.5, Neodol® 1-3, Neodol® 1-5, Iconol® DA-4, Alfonic® 810-2 Ethoxylate, and/or Alfonic® 610-3.5 Ethoxylate) were evaluated against a solvent or water-base formulation of a $C_{18}$ film-forming chemical (i.e., Agnique® MMF) in a series of shallow-water bioassays against larvae of Anopheles or Culex larvae (Table 10). Bioassays were conducted in glass pans (33.0×22.9×5.1 cm) containing 2000 ml (3.8 cm depth) of fresh water (water purified by reverse osmosis filtration) and 10 larvae (3 replications/film-forming chemical(s). Film-forming chemical formulations were applied to the water surface with a glass pipette (0.1 ml). Larvae were fed ground rabbit chow or liver powder throughout a test. Tests were conducted in a room maintained at 26–27° C.

In general, results of comparative bioassays also showed that $C_6$–$C_{11}$ alcohol ethoxylate solvent or water-base formulations performed significantly better as mosquito larvicides than a solvent or water-base formulation of the $C_{18}$ alcohol ethoxylate Agnique® MMF when evaluated over a 1 to 3 day test period. Dramatic differences in larvicidal efficacy between the water-base $C_6$–$C_{11}$ alcohol ethoxylate mixtures and the water-base formulation of the $C_{18}$ alcohol ethoxylate Agnique® MMF were observed against Culex larvae.

It should be noted that the viscosity of several $C_6$–$C_{11}$ alcohol ethoxylate water-base mixtures applied at 3.0 gal/acre (0.7 gal/acre film-forming chemicals) indicated that total application rates of 5.0 to 7.0 gal/acre would improve the flowability of certain water-base film-forming chemicals or mixtures applied at 0.7 gal/acre active(s). High shear mechanical mixing, mixing valves, or injection systems may be required to adequately spray the aqueous film-forming agent(s) on an operational basis. Also, water-base formulations may require the addition of a foam-reducing or prevention agent such as a silicone derivative.

EXAMPLE 13

The spreading rate of a surface active film-forming chemical is important in determining the efficacy of penetration through surface and emergent aquatic vegetation and the efficiency in which other chemical or microbial pesticides that are mixed with a film-forming agent will be dispersed or translocated from one or more point sources throughout an aquatic habitat when applied by ground or aerial application. The spreading rate in conjunction with larvicidal/pupicidal efficacy will be important in selection of the optimum film-forming agent(s) for use in aquatic pest management.

The comparative spreading rates between a $C_{18}$ alcohol ethoxylate (Agnique® MMF) and a $C_9/C_{10}C_{11}$ alcohol ethoxylate (Neodol® 91-2.5) or $C_{11}$ alcohol ethoxylate (Neodol® 1-3) or mixtures of the Neodol® products and a written description of the test chambers and protocol are presented in Table 11. In general, each film-forming chemical or formulation was applied to the surface of distilled water at a rate of 0.02 ml with a 0.2 ml glass pipette (3 replications/film-forming chemical). The time (seconds) required to push the styrofoam float to the opposite wall of the glass pan was recorded with a stop watch.

Results indicated that the rate of spreading of the Neodol® products and formulations was twice as fast as Agnique® MMF. This suggested that the $C_9$–$C_{11}$ alcohol ethoxylates would be twice as effective as the $C_{18}$ alcohol ethoxylate in spreading over the surface of a habitat and/or translocating one or more secondary pesticides throughout an aquatic habitat.

SUMMARY (EXAMPLES 1–13)

In general, results of a series of bioassay examples to demonstrate the mosquito-controlling efficacy of selected $C_6$–$C_{11}$ alcohol ethoxylates, alcohol ethoxylate mixtures, solvent or aqueous alcohol ethoxylate formulations indicated that one or more of these products or product formulations can be used to effectively control 1st to 4th instar larvae or pupae of several species of mosquitoes in a variety of water qualities at low application rates. Comparative mosquito-controlling bioassays between $C_{10}$, $C_{11}$, $C_6$–$C_{10}$, $C_8$–$C_{10}$, or $C_9$–$C_{11}$ alcohol ethoxylates permutations or combinations or mixtures of these technical, solvent or water-base alcohol ethoxylates and $C_{12}$–$C_{13}$, $C_{12}$–$C_{13}$–$C_{14}$–$C_{15}$, or $C_{18}$ alcohol ethoxylates further indicated that $C_6$–$C_{11}$ products, mixtures or formulations performed significantly better than the $C_{12}$–$C_{18}$ products at similar application rates.

The efficacy of selected $C_6$–$C_{11}$ alcohol ethoxylates in entrapping and killing (i.e., drowning) ovipositing female and resting male mosquitoes was also demonstrated. The ovicidal or eclosion-inhibiting effect of $C_6$–$C_{11}$ alcohol ethoxylates was also suggested.

TABLE 1

Comparative Mosquito-Controlling Efficacy of the Film-Forming Agents Agnique ® MMF and Neodol ® 91-2.5[1]

| Mosquito Species | Larval Instar | Water Quality | Film Type | % Control of Larvae at Indicated Posttreatment Time Period (Days)[2] | | | | | | | | | | | |
|---|---|---|---|---|---|---|---|---|---|---|---|---|---|---|---|
| | | | | 1 | 2 | 3 | 4 | 5 | 6 | 7 | 8 | 9 | 10 | 11 | 12 |
| An. quadrimaculatus | 1st | Brackish[3] | Neodol ® | 76.7 | 93.3 | 93.3 | 93.3 | 93.3 | 93.3 | 100 | — | — | — | — | — |
| | | | Agnique ® | 3.3 | 76.6 | 93.3 | 93.3 | 93.3 | 93.3 | 93.3 | 93.3 | 93.3 | 96.7 | 96.7 | 96.7 |
| An. quadrimaculatus | 2nd | Brackish | Neodol ® | 100 | — | — | — | — | — | — | — | — | — | — | — |
| | | | Agnique ® | 0 | 0 | 0 | 0 | 0 | 0 | 0 | 3.3 | 3.3 | 3.3 | 6.7 | 13.3 |
| An. quadrimaculatus | 3rd | Brackish | Neodol ® | 100 | — | — | — | — | — | — | — | — | — | — | — |
| | | | Agnique ® | 53.3 | 80 | 86.7 | 90 | 100 | — | — | — | — | — | — | — |

TABLE 1-continued

Comparative Mosquito-Controlling Efficacy of the Film-Forming Agents Agnique ® MMF and Neodol ® 91-2.5[1]

| | | | | | | | | | | | | | |
|---|---|---|---|---|---|---|---|---|---|---|---|---|---|
| An. quadrimaculatus | 4th | Brackish | Neodol ® | 90 | 100 | — | — | — | — | — | — | — | — | — |
| | | | Agnique ® | 40 | 56.7 | 60 | 60 | 60 | 66.7 | 70 | 73.3 | 86.7 | 96.7 | 96.7 | 100 |
| Ae. aegypti | 1st | Fresh[4] | Neodol ® | 100 | — | — | — | — | — | — | — | — | — | — |
| | | | Agnique ® | 0 | 0 | 0 | 0 | 0 | 3.3 | 3.3 | 20 | 23.3 | 26.7 | 30 | 33.3 |
| Ae. aegypti | 2nd | Fresh | Neodol ® | 100 | — | — | — | — | — | — | — | — | — | — |
| | | | Agnique ® | 53.3 | 96.7 | 100 | — | — | — | — | — | — | — | — |
| Ae. aegypti | 3rd | Fresh | Neodol ® | 100 | — | — | — | — | — | — | — | — | — | — |
| | | | Agnique ® | 0 | 0 | 33.3 | 36.7 | 40 | 40 | 40 | 50 | 50 | 56.7 | 60 | 67.7 |
| Ae. taeniarhynchus | 2nd | Brackish | Neodol ® | 100 | — | — | — | — | — | — | — | — | — | — |
| | | | Agnique ® | 3.3 | 10 | 56.7 | 63.3 | 66.7 | 66.7 | 66.7 | 73.3 | 76.7 | 80 | 83.3 | 90 |
| Cx. quinquefasciatus | 2nd | Fresh | Neodol ® | 93.3 | 100 | — | — | — | — | — | — | — | — | — |
| | | | Agnique ® | 3.3 | 23.3 | 26.7 | 26.7 | 46.7 | 50 | 50 | 53.3 | 53.3 | 53.3 | 53.3[6] | 56.7[7] |
| Cx. quinquefasciatus | 3rd | Fresh | Neodol ® | 100 | — | — | — | — | — | — | — | — | — | — |
| | | | Agnique ® | 0 | 0 | 3.3 | 13.3 | 30 | 30 | 30 | 70 | 93.3 | 100 | — | — |

| Mosquito Species | Larval Instar | Water Quality | Film Type | % Control of Larvae at Indicated Posttreatment Time Period (Days)[2] | | | | | | | |
|---|---|---|---|---|---|---|---|---|---|---|---|
| | | | | 13 | 14 | 15 | 16 | 17 | 18 | 19 | 20 |
| An. quadrimaculatus | 1st | Brackish[3] | Neodol ® | — | — | — | — | — | — | — | — |
| | | | Agnique ® | 96.7 | 96.7 | 96.7 | 96.7 | 96.7 | 96.7 | 100 | — |
| An. quadrimaculatus | 2nd | Brackish | Neodol ® | — | — | — | — | — | — | — | — |
| | | | Agnique ® | 13.3 | 13.3 | 26.7 | 53.3 | 53/3 | 73.3 | 93.3 | 100 |
| An. quadrimaculatus | 3rd | Brackish | Neodol ® | — | — | — | — | — | — | — | — |
| | | | Agnique ® | — | — | — | — | — | — | — | — |
| An. quadrimaculatus | 4th | Brackish | Neodol ® | — | — | — | — | — | — | — | — |
| | | | Agnique ® | — | — | — | — | — | — | — | — |
| Ae. aegypti | 1st | Fresh[4] | Neodol ® | — | — | — | — | — | — | — | — |
| | | | Agnique ® | 36.7 | 40 | 46.7 | 50 | 53.3 | 56.7 | 56.7 | 66.7[5] |
| Ae. aegypti | 2nd | Fresh | Neodol ® | — | — | — | — | — | — | — | — |
| | | | Agnique ® | — | — | — | — | — | — | — | — |
| Ae. aegypti | 3rd | Fresh | Neodol ® | — | — | — | — | — | — | — | — |
| | | | Agnique ® | 73.3 | 80 | 83.3 | 86.7 | 93.3 | 93.3 | 100 | |
| Ae. taeniarhynchus | 2nd | Brackish | Neodol ® | — | — | — | — | — | — | — | — |
| | | | Agnique ® | 90 | 96.7 | 96.7 | 96.7 | 96.7 | 96.7 | 100 | — |
| Cx. quinquefasciatus | 2nd | Fresh | Neodol ® | — | — | — | — | — | — | — | — |
| | | | Agnique ® | 73.3[8] | — | — | — | — | — | — | — |
| Cx. quinquefasciatus | 3rd | Fresh | Neodol ® | — | — | — | — | — | — | — | — |
| | | | Agnique ® | — | — | — | — | — | — | — | — |

[1]Technical film-forming agents applied to water surface at ca. 0.7 ± 0.05 gal/acre
[2]10 larvae/crystallizing dish (3 replications/test); 0–3.3% mortality in controls (3 replications/test series)
[3]10% seawater (Instant Ocean ®/distilled water)
[4]Water purified by reverse osmosis filtration
[5]76.7, 83.3, 86.7, 86.7, 86.7, 86.7, 86.7, 93.3, and 100% control at 21–29 days, respectively
[6]3 adults emerged
[7]2 adults emerged
[8]3 adults emerged

TABLE 2

Effect of Application Rate on the Mosquito-Controlling Efficacy of Neodol ® 91-2.5

| Mosquito Species | Larval Instar | Water quality | Application Rate (Gal/Acre) | % Control of Larvae at Indicated Posttreatment Time Period (Days)[1] | | | | | | | | | |
|---|---|---|---|---|---|---|---|---|---|---|---|---|---|
| | | | | 1 | 2 | 3 | 4 | 5 | 6 | 7 | 8 | 9 | 10 |
| Aedes aegypti | 1st | Fresh[2] | 0.50 | 6.7 | 16.7 | 16.7 | 30 | 36.7 | 43.3 | 43.3 | 43.3 | 43.3 | 46.7 |
| | | | 0.62 | 73.3 | 86.7 | 86.7 | 86.7 | 86.7 | 86.7 | 86.7 | 86.7 | 86.7 | 86.7 |
| | | | 0.71 | 100 | — | — | — | — | — | — | — | — | — |
| Aedes aegypti | 4th | Fresh | 0.50 | 0 | 3.3 | 3.3 | 3.3 | 10 | 13.3 | 13.3 | 13.3 | 20 | 23.3 |
| | | | 0.71 | 53.3 | 70 | 100 | — | — | — | — | — | — | — |
| Anopheles quadrimaculatus | 2nd | Brackish[3] | 0.50 | 16.7 | 30 | 43.3 | 50 | 50 | 60 | 60 | 66.7 | 70 | 70 |
| | | | 0.71 | 86.7 | 96.7 | 96.7 | 96.7 | 96.7 | 96.7 | 96.7 | 100 | — | — |
| Anopheles quadrimaculatus | 3rd | Brackish | 0.50 | 36.7 | 63.3 | 90 | 93.3 | 93.3 | 93.3 | 96.7 | 96.7 | 100 | — |
| | | | 0.62 | 100 | — | — | — | — | — | — | — | — | — |
| | | | 0.71 | 100 | — | — | — | — | — | — | — | — | — |
| Anopheles quadrimaculatus | 4th | Brackish | 0.50 | 3.3 | 6.7 | 13.3 | 20 | 33.3 | 43.3 | 43.3 | 43.3 | 46.7 | 50[8] |
| | | | 0.62 | 56.7 | 56.7 | 73.3 | 73.3 | 83.3 | 86.7 | 86.7[9] | — | — | — |
| | | | 0.71 | 100 | — | — | — | — | — | — | — | — | — |
| Culex quinquefasciatus | 3rd | Brackish | 0.50 | 10 | 16.7 | 20 | 43.3 | 53.3 | 73.3 | 76.7 | 76.7 | 76.7 | 76.7 |
| | | | 0.71 | 100 | — | — | — | — | — | — | — | — | — |

TABLE 2-continued

Effect of Application Rate on the Mosquito-Controlling Efficacy of Neodol ® 91-2.5

| Mosquito Species | Larval Instar | Water quality | Application Rate (Gal/Acre) | % Control of Larvae at Indicated Posttreatment Time Period (Days)[1] | | | | |
|---|---|---|---|---|---|---|---|---|
| | | | | 11 | 12 | 13 | 14 | 15 |
| Aedes aegypti | 1st | Fresh[2] | 0.50 | 53.3 | 53.3 | 53.3 | 53.3 | 56.7[4] |
| | | | 0.62 | 93.3 | 96.7[5] | — | — | — |
| | | | 0.71 | — | — | — | — | — |
| Aedes aegypti | 4th | Fresh | 0.50 | 23.3 | 30 | 33.3[6] | — | — |
| | | | 0.71 | — | — | — | — | — |
| Anopheles quadrimaculatus | 2nd | Brackish[3] | 0.50 | 70 | 80 | 86.7[7] | — | — |
| | | | 0.71 | — | — | — | — | — |
| Anopheles quadrimaculatus | 3rd | Brackish | 0.50 | — | — | — | — | — |
| | | | 0.62 | — | — | — | — | — |
| | | | 0.71 | — | — | — | — | — |
| Anopheles quadrimaculatus | 4th | Brackish | 0.50 | — | — | — | — | — |
| | | | 0.62 | — | — | — | — | — |
| | | | 0.71 | — | — | — | — | — |
| Culex quinquefasciatus | 3rd | Brackish | 0.50 | 76.7 | 83.3 | 83.3 | 83.3 | 90[10] |
| | | | 0.71 | — | — | — | — | — |

[1]10 larvae/crystallizing dish (0.50 gal/acre), 800 ml beaker (0.62 gal/acre) or 400 ml beaker (0.71 gal/acre) (3 replications/test); 0–3.3% mortality in controls (3 replications/test series)
[2]Water purified by reverse osmosis filtration
[3]10% seawater (Instant Ocean ®/distilled water)
[4,5,6,7,8,9,10]43.3%, 3.3%, 66.7%, 13.3%, 50%, 13.3%, and 10% of test populations emerged as adults, respectively

TABLE 3

Comparative Mosquito-Controlling Efficacy of Neodol ® 91-2.5 and Solvent Formulations of Neodol ® 91-2.5[1]

| Mosquito Species (Instar/Water Quality) | Total Application Rate (Gal/Acre) | Neodol ® Application Rate (Gal/Acre) | Film Formulation (% Components) | % Control of Larvae[2] at Indicated Posttreatment Time Period (Hours[3]/Days[4]) | | | | | | | | | | | |
|---|---|---|---|---|---|---|---|---|---|---|---|---|---|---|---|
| | | | | 1 | 2 | 3 | 4 | 1 | 2 | 3 | 4 | 5 | 6 | 7 | 8 |
| Anopheles quadrimaculatus (2nd/Brackish) | 0.71 | 0.71 | Neodol ® (100) | 13.3 | 40 | 53.3 | 70 | 70 | 100 | — | — | — | — | — | — |
| | 0.68 | 0.51 | Neodol ®/Methanol (75/25) | 6.7 | 33.3 | 46.7 | 56.7 | 56.7 | 86.7 | 86.7 | 86.7 | 86.7 | 86.7 | 90 | 90 |
| | 0.62 | 0.31 | Neodol ®/Methanol (50/50) | 6.7 | 10 | 16.7 | 23.3 | 30 | 66.7 | 86.7 | 90 | 90 | 90 | 90 | 90 |
| | 0.65 | 0.49 | Neodol ®/Ethanol (75/25) | 10 | 26.7 | 36.7 | 40 | 43.3 | 80 | 80 | 80 | 80 | 80 | 83.3 | 83.3 |
| | 0.62 | 0.31 | Neodol ®/Ethanol (50/50) | 6.7 | 6.7 | 6.7 | 6.7 | 6.7 | 13.3 | 33.3 | 60 | 73.3 | 76.7 | 80 | 80 |
| Anopheles quadrimaculatus (3rd/Brackish) | 0.71 | 0.71 | Neodol ® (100) | 3.3 | 40 | 60 | 70 | 100 | — | — | — | — | — | — | — |
| | 0.65 | 0.49 | Neodol ® Propanol (75/25) | 10 | 43.3 | 43.3 | 43.3 | 66.7 | 76.7 | 76.7 | 86.7 | 86.7 | 90 | 90 | 90 |
| | 0.60 | 0.30 | Neodol ® Propanol (50/50) | 3.3 | 26.7 | 46.7 | 53.3 | 66.7 | 66.7 | 80 | 86.7 | 86.7 | 86.7 | 90 | 93.3 |
| | 0.65 | 0.49 | Neodol ®/Ethanol (75/25) | 10 | 13.3 | 43.3 | 60 | 90 | 93.3 | 96.7 | 100 | — | — | — | — |
| | 0.62 | 0.31 | Neodol ®/Ethanol (50/50) | 16.7 | 40 | 40 | 53.3 | 73.3 | 76.7 | 83.3 | 86.7 | 90 | 93.3 | 93.3 | 93.3 |
| | 0.68 | 0.51 | Neodol ®/Methanol (75/25) | 20 | 43.3 | 73.3 | 73.3 | 86.7 | 100 | — | — | — | — | — | — |
| | 0.62 | 0.31 | Neodol ®/Methanol (50/50) | 26.7 | 30 | 63.3 | 63.3 | 96.7 | 100 | — | — | — | — | — | — |
| Anopheles quadrimaculatus (4th/Brackish) | 0.71 | 0.71 | Neodol ® (100) | 33.3 | 83.3 | 90 | 93.3 | 100 | — | — | — | — | — | — | — |
| | 0.65 | 0.49 | Neodol ®/Propanol | 33.3 | 66.7 | 93.3 | 96.7 | 100 | — | — | — | — | — | — | — |

TABLE 3-continued

Comparative Mosquito-Controlling Efficacy of Neodol ® 91-2.5 and Solvent Formulations of Neodol ® 91-2.5[1]

| Mosquito Species (Instar/Water Quality) | Total Application Rate (Gal/Acre) | Neodol ® Application Rate (Gal/Acre) | Film Formulation (% Components) | | | | | | | | | | | |
|---|---|---|---|---|---|---|---|---|---|---|---|---|---|---|
| | 0.60 | 0.30 | Neodol ®/Propanol (75/25) | 53.3 | 73.3 | 73.3 | 73.3 | 73.3 | 80 | 80 | 83.3 | 83.3 | 83.3 | 83.3 | 90 |
| | 0.65 | 0.49 | Neodol ®/Ethanol (75/25) | 30 | 66.7 | 76.7 | 93.3 | 100 | — | — | — | — | — | — | — |
| | 0.62 | 0.31 | Neodol ®/Ethanol (50/50) | 43.3 | 50 | 83.3 | 96.7 | 100 | — | — | — | — | — | — | — |
| | 0.68 | 0.51 | Neodol ®/Methanol (75/25) | 50 | 66.7 | 96.7 | 96.7 | 100 | — | — | — | — | — | — | — |
| | 0.62 | 0.31 | Neodol ®/Methanol (50/50) | 33.3 | 40 | 40 | 63.3 | 66.7 | 66.7 | 70 | 86.7 | 90 | 100 | — | — |
| Culex quinquefasciatus (3rd/Brackish) | 0.71 | 0.71 | Neodol ® (100) | 23.3 | 36.7 | 40 | 53.3 | 100 | — | — | — | — | — | — | — |
| | 0.65 | 0.49 | Neodol ®/Propanol (75/25) | 23.3 | 36.7 | 56.7 | 63.3 | 90 | 96.7 | 96.7 | 100 | — | — | — | — |
| | 0.60 | 0.30 | Neodol ®/Propanol (50/50) | 30 | 30 | 30 | 40 | 73.3 | 86.7 | 86.7 | 100 | — | — | — | — |
| | 0.68 | 0.51 | Neodol ®/Methanol (75/25) | 20 | 20 | 46.7 | 46.7 | 83.3 | 90 | 90 | 100 | — | — | — | — |
| | 0.62 | 0.31 | Neodol ®/Methanol (50/50) | 13.3 | 23.3 | 40 | 40 | 93.3 | 93.3 | 96.7 | 100 | — | — | — | — |
| Culex quinquefasciatus (3rd/Fresh) | 0.71 | 0.71 | Neodol ®/(100) | 0 | 0 | 0 | 16.7 | 86.7 | 86.7 | 90 | 93.3 | 93.3 | 96.7 | 96.7 | 96.7 |
| | 0.65 | 0.49 | Neodol ®/Ethanol (75/25) | 0 | 0 | 0 | 0 | 100 | — | — | — | — | — | — | — |
| | 0.62 | 0.31 | Neodol ®/Ethanol (50/50) | 0 | 0 | 0 | 0 | 53.3 | 56.7 | 73.3 | 76.7 | 76.7 | 86.7 | 86.7 | 86.7 |
| Culex quinquefasciatus (4th/Fresh) | 0.71 | 0.71 | Neodol ®/(100) | 0 | 0 | 0 | 30 | 90 | 93.3 | 93.3 | 96.7 | 96.7 | 96.7 | 96.7 | 96.7 |
| | 0.65 | 0.49 | Neodol ®/Ethanol (75/25) | 0 | 0 | 0 | 0 | 86.7 | 90 | 90 | 90 | 90 | 93.3 | 93.3 | 96.7 |
| | 0.62 | 0.31 | Neodol ®/Ethanol (50/50) | 0 | 0 | 0 | 3.3 | 53.3 | 70 | 76.6 | 83.3 | 86.7 | 90 | 90 | 90 |
| Culex quinquefasciatus (4th/Fresh) | 0.71 | 0.71 | Neodol ®/Propanol (75/25) | 13 | 26.7 | 70 | 83.3 | 100 | — | — | — | — | — | — | — |
| | | | | 10 | 13.3 | 16.7 | 36.7 | 70 | 70 | 100 | — | — | — | — | — |
| | 0.60 | 0.30 | Neodol ®/Propanol (50/50) | 10 | 10 | 10 | 13.3 | 36.7 | 36.7 | 36.7 | 70 | 73/3[7] | — | — | — |
| | 0.68 | 0.51 | Neodol ®/Methanol (75/25) | 13.3 | 20 | 56.7 | 73.3 | 100 | — | — | — | — | — | — | — |
| | 0.62 | 0.31 | Neodol ®/Methanol (50/50) | 16.7 | 30 | 70 | 70 | 83.3 | 96.7 | 100 | — | — | — | — | — |

| Mosquito Species (Instar/Water Quality) | Total Application Rate (Gal/Acre) | Neodol ® Application Rate (Gal/Acre) | Film Formulation (% Components) | % Control of Larvae[2] at Indicated Posttreatment Time Period (Hours[3]/Days[4]) | | | | | | | | | | | |
|---|---|---|---|---|---|---|---|---|---|---|---|---|---|---|---|
| | | | | 9 | 10 | 11 | 12 | 13 | 14 | 15 | 16 | 17 | 18 | 19 | 20 |
| Anopheles quadrimaculatus (2nd/Brackish) | 0.71 | 0.71 | Neodol ® (100) | — | — | — | — | — | — | — | — | — | — | — | — |
| | 0.68 | 0.51 | Neodol ®/Methanol (75/25) | 93.3 | 93.3 | 93.3 | 93.3 | 93.3 | 93.3 | 93.3 | 93.3 | 93.3 | 93.3 | 100 | — |
| | 0.62 | 0.31 | Neodol ®/Methanol (50/50) | 90 | 90 | 90 | 93.3 | 96.7 | 96.7 | 96.7 | 96.7 | 96.7 | 96.7 | 96.7 | 100 |
| | 0.65 | 0.49 | Neodol ®/Ethanol (75/25) | 86.7 | 86.7 | 86.7 | 90 | 90 | 90 | 90 | 90 | 93.3 | 93.3 | 100 | — |

TABLE 3-continued

Comparative Mosquito-Controlling Efficacy of Neodol ® 91-2.5 and Solvent Formulations of Neodol ® 91-2.5[1]

| Species | | | | | | | | | | | | | |
|---|---|---|---|---|---|---|---|---|---|---|---|---|---|
| | 0.62 | 0.31 | Neodol ®/Ethanol (50/50) | 83.3 | 93.3 | 93.3 | 93.3 | 100 | — | — | — | — | — |
| *Anopheles quadrimaculatus* (3rd/Brackish) | 0.71 | 0.71 | Neodol ® (100) | — | — | — | — | — | — | — | — | — | — |
| | 0.65 | 0.49 | Neodol ®/Propanol (75/25) | 90 | 90 | 93.3 | 93.3 | 96.7 | 96.7 | 96.7 | 10 | — | — |
| | 0.60 | 0.30 | Neodol ®/Propanol (50/50) | 93.3 | 93.3 | 93.3 | 93.3 | 93.3 | 93.3 | 100 | — | — | — |
| | 0.65 | 0.49 | Neodol ®/Ethanol (75/25) | — | — | — | — | — | — | — | — | — | — |
| | 0.62 | 0.31 | Neodol ®/Ethanol (50/50) | 93.3 | 96.7 | 96.7 | 96.7 | 96.7 | 96.7 | 100 | — | — | — |
| | 0.68 | 0.51 | Neodol ®/Methanol (75/25) | — | — | — | — | — | — | — | — | — | — |
| | 0.62 | 0.31 | Neodol ®/Methanol (50/50) | — | — | — | — | — | — | — | — | — | — |
| *Anopheles quadrimaculatus* (4th/Brackish) | 0.71 | 0.71 | Neodol ® (100) | — | — | — | — | — | — | — | — | — | — |
| | 0.65 | 0.49 | Neodol ®/Propanol (75/25) | — | — | — | — | — | — | — | — | — | — |
| | 0.60 | 0.30 | Neodol ®/Propanol (50/50) | 93.3 | 96.7 | 100 | — | — | — | — | — | — | — |
| | 0.65 | 0.49 | Neodol ®/Ethanol (75/25) | — | — | — | — | — | — | — | — | — | — |
| | 0.62 | 0.31 | Neodol ®/Ethanol (50/50) | — | — | — | — | — | — | — | — | — | — |
| | 0.68 | 0.51 | Neodol ®/Methanol (75/25) | — | — | — | — | — | — | — | — | — | — |
| | 0.62 | 0.31 | Neodol ®/Methanol (50/50) | — | — | — | — | — | — | — | — | — | — |
| *Culex quinquefasciatus* (3rd/Brackish) | 0.71 | 0.71 | Neodol ® (100) | — | — | — | — | — | — | — | — | — | — |
| | 0.65 | 0.49 | Neodol ®/Propanol (75/25) | — | — | — | — | — | — | — | — | — | — |
| | 0.60 | 0.30 | Neodol ®/Propanol (50/50) | — | — | — | — | — | — | — | — | — | — |
| | 0.68 | 0.51 | Neodol ®/Methanol (75/25) | — | — | — | — | — | — | — | — | — | — |
| | 0.62 | 0.31 | Neodol ®/Methanol (50/50) | — | — | — | — | — | — | — | — | — | — |
| *Culex quinquefasciatus* (3rd/Fresh) | 0.71 | 0.71 | Neodol ®/(100) | 96.7 | 96.7 | 96.7 | 96.7 | 100 | — | — | — | — | — |
| | 0.65 | 0.49 | Neodol ®/Ethanol (75/25) | — | — | — | — | — | — | — | — | — | — |
| | 0.62 | 0.31 | Neodol ®/Ethanol (50/50) | 86.7 | 90 | 93.3 | 96.7[5] | — | — | — | — | — | — |
| *Culex quinquefasciatus* (4th/Fresh) | 0.71 | 0.71 | Neodol ®/(100) | 96.7[6] | — | — | — | — | — | — | — | — | — |
| | 0.65 | 0.49 | Neodol ®/Ethanol (75/25) | 96.7 | 96.7 | 96.7 | 96.7 | 96.7 | 100 | — | — | — | — |
| | 0.62 | 0.31 | Neodol ®/Ethanol (50/50) | 90 | 93.3 | 96.7 | 100 | — | — | — | — | — | — |

TABLE 3-continued

Comparative Mosquito-Controlling Efficacy of Neodol ® 91-2.5 and Solvent Formulations of Neodol ® 91-2.5[1]

| Culex quinquefasciatus (4th/Fresh) | 0.71 | 0.71 | Neodol ®/ Propanol (75/25) | — | — | — | — | — | — | — | — | — | — | — | — |
|---|---|---|---|---|---|---|---|---|---|---|---|---|---|---|---|
|  | 0.60 | 0.30 | Neodol ®/ Propanol (50/50) | — | — | — | — | — | — | — | — | — | — | — | — |
|  | 0.68 | 0.51 | Neodol ®/ Methanol (75/25) | — | — | — | — | — | — | — | — | — | — | — | — |
|  | 0.62 | 0.31 | Neodol ®/ Methanol (50/50) | — | — | — | — | — | — | — | — | — | — | — | — |

[1] Technical Methanol, Ethanol, and 2-propanol were used as solvent examples in Neodol ® formulations
[2] 10 larvae/500 ml beaker (3 replications/test); 0–3.3% mortality in controls (3 replications/test series)
[3] First group of 1–4 indicate hours posttreatment
[4] Second group of 1–20 indicate days posttreatment
[5,6,7] 3.3%, 3.3% and 26.7% adult emergence respectively

TABLE 4

Effect of Water Volume and Depth on the Mosquito-Controlling Efficacy of Neodol ® 91-2.5 in Shallow Water Habitats[1]

| Mosquito Species | Larval Instar/ Pupae | Water Quality | Water Volume (ml)/ Depth (cm) | Application Rate (Gal/Acre) | % Control of larvae or Pupae at Indicated Posttreatment Time Period (Days)[2] | | | | | |
|---|---|---|---|---|---|---|---|---|---|---|
| | | | | | 1 | 2 | 3 | 4 | 5 | 6 |
| An. quadrimaculatus | 2nd | Brackish | 1000/1.9 | 0.7 | 100 | — | — | — | — | — |
| An. quadrimaculatus | 3rd | Brackish | 2000/3.8 | 0.7 | 83.3 | 100 | — | — | — | — |
| An. quadrimaculatus | 4th | Brackish | 2000/3.8 | 0.7 | 90 | 90 | 90 | 90 | 93.3 | 100 |
| Ae. taeniorhynchus | 1st | Brackish | 2000/3.8 | 0.5, 0.7 | 100 | — | — | — | — | — |
| Ae. taeniorhynchus | 4th | Brackish | 2000/3.8 | 0.7 | 100 | — | — | — | — | — |
| Cx. quinquefasciatus | 2nd | Fresh | 1000/1.9 | 0.5, 0.7 | 100 | — | — | — | — | — |
| Cx. quinquefasciatus | 3rd | Fresh | 1000/1.9 | 0.3, 0.5, 0.7 | 100 | — | — | — | — | — |
| Cx. quinquefasciatus | 3rd | Fresh | 2000/3.8 | 0.7 | 100 | — | — | — | — | — |
| Cx. quinquefasciatus | 4th | Fresh | 1000/1.9 | 0.3, 0.5, 0.7 | 100 | — | — | — | — | — |
| Cx. quinquefasciatus | 4th | Fresh | 2000/3.8 | 0.7 | 100 | — | — | — | — | — |
| Cx. quinquefasciatus | 4th | Fresh | 2000/3.8 | 0.5 | 93.3 | 93.3 | 96.7 | 100 | — | — |
| Cx. quinquefasciatus | Pupae | Fresh | 1000/1.9 | 0.7 | 93.3 | 100 | — | — | — | — |
| Cx. quinquefasciatus | Pupae | Fresh | 2000/3.8 | 0.7 | 90 | 93.3 | 100 | — | — | — |

[1] Technical or solvent formulations of film-forming agent applied to water surface at ca. 0.3, 0.5 or 0.7 ± 0.05 gal/acre
[2] 10 Larvae or pupae/glass pan (3 replications/test); 0–3.3% mortality in controls (3 replications/test series)

TABLE 5

Effect of Water Volume and Depth on the Mosquito-Controlling Efficacy of Neodol ® 91-2.5 in Shallow and Deep Water Habitats[1]

| Mosquito Species | Larval Instar | Water Quality | Application Rate (Gal/Acre) | Film Formulation (% Composition) | Water Volume (ml)/ Depth (cm) | % Control of Larvae at Indicated Posttreatment Time Period (Days)[2] | |
|---|---|---|---|---|---|---|---|
| | | | | | | 1 | 2 |
| Cx. quinquefasciatus | 2nd | Fresh | 0.7 | Neodol ® (100) | 1920/5.1 | 100 | — |
|  |  |  |  |  | 7580/15.2 | 76.7 | — |
|  |  |  |  |  | 16880/30.5 | 6.7 | — |
| Cx. quinquefasciatus | 4th | Fresh | 0.7 | Neodol ® (100) | 1920/5.1 | 100 | — |
|  |  |  |  |  | 7580/15.2 | 70 | 100 |
|  |  |  |  |  | 16880/30.5 | 63.3 | 100 |
| Cx. quinquefasciatus | 4th | Fresh | 0.7 | Neodol ®/ Methanol (75/25) | 1920/5.1 | 100 | — |
|  |  |  |  |  | 7580/15.2 | 100 | — |
|  |  |  |  |  | 16880/30.5 | 100 | — |

[1] Technical or solvent formulations of film-forming agent applied to water surface at ca. 0.7 ± 0.05 gal/acre
[2] 10 Larvae/bucket (3 replications/water level); 0% mortality in controls (3 replications/test series)

TABLE 6

Comparative Mosquito-Controlling Efficacy of Several Film-Forming Agents in Shallow Water Habitats[1]

| Mosquito Species | Larval Instar | Water Quality | Application Rate (Gal/Acre) | Film Description/ Formulation (% Composition) | % Control of Larvae at Indicated Posttreatment Time Period (Days)[2] | |
|---|---|---|---|---|---|---|
| | | | | | 1 | 2 |
| Ae. aegypti | 4th | Fresh | 0.7 | Neodol ® 1-3 (100) | 100 | — |
| | | | | Neodol ® 91-2.5/Neodol ® 1-3 (75125) | 63.3 | — |
| | | | | Neodol ® 23-1 (100) | 10 | — |
| | | | | Neodol ® 25-3 (100) | 16.7 | — |
| An. quadrimaculatus | 3rd | Fresh | 0.3 | Neodol ® 1-3 (100) | 36.7 | — |
| | | | 0.5 | Neodol ® 1-3 (100) | 73.3 | — |
| | | | 0.7 | Neodol ® 1-3 (100) | 100 | — |
| | | | 0.3 | Neodol ® 91-2.5/Neodol ® 1-3 (75/25) | 66.7 | 100 |
| | | | 0.5 | Neodol ® 91-2.5/Neodol ® 1-3 (75/25) | 100 | — |
| | | | 0.7 | Neodol ® 91-2.5/Neodol ® 1-3 (75/25) | 100 | — |
| Cx. quinquefasciatus | 2nd | Fresh | 0.7 | Neodol ® 91-2.5 (100) | 100 | — |
| | | | | Neodol ® 91-2.5/Neodol ® 1-3 (75/25) | 100 | — |
| Cx. quinquefasciatus | 3rd | Fresh | 0.7 | Neodol ® 91-2.5 (100) | 100 | — |
| | | | | Neodol ® 1-3 (100) | 100 | — |
| | | | | Neodol ® 91-2.5/Neodol ® 1-3 (75/25) | 100 | — |
| | | | | Neodol ® 25-3 (100) | 3.3 | — |
| Cx. quinquefasciatus | 4th | Fresh | 0.7 | Neodol ® 91-2.5 (100) | 100 | — |
| | | | | Neodol ® 1-3 (100) | 100 | — |
| | | | | Neodol ® 25-3 (100) | 26.7 | — |

[1]Technical film-forming agents/formulation applied to water surface at ca. 7 ± 0.05 gal/acre
[2]10 Larvae/glass pan - 2000 ml water/3.8 cm depth; 0% mortality in control (3 replications/test series)

TABLE 7

Comparative Mosquito-Controlling Efficacy of Several Film-Forming Agents in Deep Water Habitats

| Mosquito Species | Larval Instar | Water Quality | Application Rate (Gal/Acre) | Film Type/ Formulation (% Composition) | % Control of Larvae at Indicated Posttreatment Time Period (Days)[2] | | | | | |
|---|---|---|---|---|---|---|---|---|---|---|
| | | | | | 1 | 2 | 3 | 4 | 5 | 6 |
| An. quadrimaculatus | 3rd | Fresh | 0.7 | Neodol ® 91-2.5 (100) | 100 | — | — | — | — | — |
| | | | | Neodol ® 91-2.5/Neodol ® 1-3 (75/25) | 100 | — | — | — | — | — |
| | | | | Neodol ® 1-3 (100) | 73.3 | — | — | — | — | — |
| An. quadrimaculatus | 4th | Fresh | 0.7 | Neodol ® 91-2.5 (100) | 100 | — | — | — | — | — |
| | | | | Neodol ® 91-2.5/Neodol ® 1-3 (75/25) | 100 | — | — | — | — | — |
| | | | | Neodol ® 1-3 (100) | 100 | — | — | — | — | — |
| Cx. quinquefasciatus | 4th | Fresh | 0.7 | Neodol ® 91-2.5 (100) | 80 | 93.3 | 96.7 | 96.7 | 96.7 | 100 |
| | | | | Neodol ® 91-2.5/Neodol ® 1-3 (75/25) | 100 | — | — | — | — | — |
| | | | | Neodol ® 1-3 (100) | 93.3 | 93.3 | 93.3 | 93.3 | 93.3 | 100 |
| | | | | Neodol ® 25-3 (100) | 60 | 70 | 70 | 73.3 | 83.3 | 83.3[3] |
| | | | | Neodol ® 23-1 (100) | 53.3 | 56.7 | 56.7 | 56.7 | 63.3 | 63.3[4] |
| Cx. quinquefasciatus | 4th | Fresh | 0.7 | Neodol ® 91-2.5 (100) | 100 | — | — | — | — | — |
| | | | | Neodol ® 91-2.5/Neodol ® 1-3 (75/25) | 100 | — | — | — | — | — |
| | | | | Neodol ® 91-2.5/Neodol ® 23-1 (75/25) | 60 | — | — | — | — | — |
| | | | | Neodol ® 91-2.5/Neodol ® 25-3 (75/25) | 63.3 | — | — | — | — | — |
| | | | | Neodol ® 91-2.5/Neodol ® 23-3 (75/25) | 90 | — | — | — | — | — |
| | | | | Agnique ® MMF (100) | 43.3 | — | — | — | — | — |

[1]Technical film-forming agents/formulations applied to water surface at ca. 0.7 ± 0.05 gal/acre
[2]Larvae/bucket - 16,880 ml water/30.5 cm depth; 0% mortality in controls (3 replications/test series)
[3]16.7% adults emerged
[4]36.7% adults emerged

TABLE 8

Adult Entrapment and Oviposition Inhibition Potential of Selected Film-Forming Agents or Formulations

| Mosquito Species Quality | Water Quality | Film Type/ Formulation (% Composition) | Application Rate (Gal/Acre) | Average No. Adults in Test (T) or Control © | | Average No. Entrapped Adults in Test (T) or Control © | | Average No. Egg Rafts in Test (T) or Control © |
|---|---|---|---|---|---|---|---|---|
| | | | | Males | Females | Males | Females | |
| Cx. quinquefasciatus[1] | Fresh | Neodol ® 91-2.5 (100) | 0.7 | 65(T) 67© | 31(T) 30© | 4(T) 3© | 8(T) <1© | <1(T) 16© |
| Cx. quinquefasciatus[2] | Fresh | Neodol ® 91-2.5/ Neodol ® 1-3 (75/25) | 0.7 | 150(T) 167© | 60(T) 60© | 17(T) 2© | 6(T) 1© | 9(T) 29© |

[1]100 pupae/crystallizing dish (3 replications/film type or control); cages egged 5 days post-bloodfeeding
[2]250 pupae/crystallizing dish (3 replications/film type or control); cages egged 5 days post-bloodfeeding

TABLE 9

Comparative Mosquito-Controlling Efficacy of Several Film-Forming Chemicals or Formulations in Shallow Water Habitats[1]

| Mosquito Species | Larval Instar | Water Quality | Film Description/ Application Rate (Gal/Acre) | Formulation (% Composition) | % Control of Larvae at Indicated Posttreatment Time Period (Days)[2] 1 |
|---|---|---|---|---|---|
| Ae. aegypti | 2nd | Fresh | 0.7 | Neodol ® 91-2.5 (100) | 100 |
| | | | | Neodol ® 1-3 (100) | 100 |
| | | | | Neodol ® 23-1 (100) | 66.7 |
| | | | | Neodol ® 1-3/ Neodol ® 91-2.5 (75/25) | 100 |
| | | | | Neodol ® 1-3/ Neodol ® 91-2.5 (50/50) | 100 |
| | | | | Neodol ® 91-2.5/ Neodol ® 1-3 (75/25) | 100 |
| Cx. quinquefasciatus | 2nd | Fresh | 0.7 | Agnique ® MMF (100) | 16.7 |
| | | | | Neodol ® 91-2.5 (100) | 100 |
| | | | | Neodol ® 1-3 (100) | 100 |
| | | | | Neodol ® 1-3 Neodol ® 91-2.5 (75/25) | 100 |
| Cx. quinquefasciatus | 4th | Fresh | 0.7 | Neodol ® 91-2.5/ Neodol ® 1-3 (75/25) | 100 |
| | | | | Neodol ® 91-2.5/ Neodol ® 1-5 (75/25) | 100 |
| | | | | Neodol ® 1-3/ Neodol ® 1-5 (75/25) | 100 |
| | | | | Neodol ® 91-2.5/ Iconol ® DA-4 (75/25) | 100 |

[1]Technical film-forming agents/formulations applied to water surface at ca. 0.7 ± 0.05 gal/acre
[2]10 Larvae/glass pan (3 replications/test); 0% mortality in controls (3 replications/test series)

TABLE 10

Comparative Mosquito-Controlling Efficacy Between $C_6$–$C_{11}$ and $C_{18}$ Film-Forming Chemical Formulations in Shallow-Water Habitat[1]

| Mosquito Species | Larval Instar | Water Quality | Film Application Rate/Total Rate (Gal/Acre) | Film Description/ Formulation (% Composition) | % Control of Larvae at Indicated Posttreatment Time Period (Days)[2] | | |
|---|---|---|---|---|---|---|---|
| | | | | | 1 | 2 | 3 |
| An. quadrimaculatus | 3rd | Fresh | 0.51/0.7 | Agnique ® MMF/Methanol (75/25) | 46.7 | 73.3 | 100 |
| | | | | Neodol ® 1-3/Methanol (75/25) | 86.7 | 100 | — |
| Cx. quinquefasciatus | 2nd | Fresh | 0.7/3.0 | Agnique ® r MMF (100) | 10 | — | — |
| | | | | Neodol ® 1-3/Neodol ® 1-5/ Neodol ® 91-2.5 (40/30/30) | 100 | — | — |
| | | | | Neodol ® 1-3/Neodol ® 1-5/ Neodol ® 91-2.5 (50/30/20) | 100 | — | — |
| | | | | Neodol ® 1-3/Neodol ® 1-5/ Neodol ® 91-2.5 (50/20/30) | 100 | — | — |
| | | | | Neodol ® 1-3/Neodol ® 1-5/ Neodol ® 91-2.5/Iconol ® DA-4 (50/25/15/10) | 100 | — | — |
| | | | | Neodol ® 1-3/Neodol ® 1-5/ Neodol ® 91-2.5/Alfonic ® 610-3.5 (50/25/15/10) | 100 | — | — |
| | | | | Neodol ® 1-3/Neodol ® 91-2.5/ | 100 | — | — |

TABLE 10-continued

Comparative Mosquito-Controlling Efficacy Between $C_6$–$C_{11}$ and $C_{18}$ Film-Forming Chemical Formulations in Shallow-Water Habitat[1]

| Mosquito Species | Larval Instar | Water Quality | Film Application Rate/Total Rate (Gal/Acre) | Film Description/ Formulation (% Composition) | % Control of Larvae at Indicated Posttreatment Time Period (Days)[2] | | |
|---|---|---|---|---|---|---|---|
| | | | | | 1 | 2 | 3 |
| Cx. quinquefasciatus | 2nd | Fresh | 0.7/3.0 | Iconol ® DA-4/Alfonic ® 610-3.5(40/40/10/10) | | | |
| | | | | Agnique ® MMF (100) | 10 | — | — |
| | | | | Neodol ® 1-3/Iconol ® DA4 (75/25) | 93.3 | — | — |
| | | | | Alfonic ® 810-2/Alfonic ® 610-3.5/ Neodol ® 1-5 (50/20/30) | 100 | — | — |
| | | | | Neodol ® 1-3/Neodol ® 1-5/ Iconol ® DA-4 (50/30/20) | 100 | — | — |
| | | | | Neodol ® 1-3/Neodol ® 91-2.5 Alfonic ® 810-2 (30/30/40) | 100 | — | — |
| Cx. quinquefasciatus | 3rd | Fresh | 0.7/3.0 | Agnique ® MMF (100) | 0 | — | — |
| | | | | Alfonic ® 810-2/Alfonic ® 610-3.5/ Neodol ® 91-2.5/Neodol ® 1-31 Neodol ® 1-5/Iconol ® DA-4 (20/10/20/20/15/15) | 100 | — | — |
| | | | | Alfonic ® 810-2/Alfonic ® 610-3.5/ Neodol ® 91-2.5/Neodol ® 1-3/ Iconol ® DA-4 (10/25/25/25/15) | 100 | — | — |

[1]Solvent (i.e., Methanol) formulations of film-forming agents applied against Anopheles larvae and water-base formulations of film-forming agent applied against Culex larvae at total application rates of 0.7 and 3.0 gal/acre, respectively. Film-forming agents or mixtures of agents were applied in solvent or water at rates of ca. 0.5 or 0.7 gal/acre, respectively
[2]10 larvae/glass pan-2000 ml water/3.8 cm depth; (3 replications/test formulation); 0% mortality in controls (3 replications/test formulation)

TABLE 11

Comparative Spreading Rates of Film-Forming Agents[1]

| | Agnique ® MMF | Neodol ® 1-3 | Neodol ® 91-2.5 | Neodol ® 1-3 50% Neodol ® 91-2.5 50% | Neodol ® 1-3 75% Neodol ® 91-2.5 25% |
|---|---|---|---|---|---|
| Seconds | 2 | 1 | 1 | 1 | 1 |
| | 2 | 1 | 1 | 1 | 1 |
| | 2 | 1 | 1 | 1 | 1 |

The apparatus for testing the comparative spreading rates of film-forming agents comprised a glass pan of 33×21.6 cm. A styrofoam strip (18×1 cm) was placed with an edge 3 cm from one of the width edges (21.6 cm) of the glass pan, forming a section separated from the remainder of the pan. The film was applied within the formed section, in the geometric center of the section. The surface area was about 0.0993 m$^2$, the water depth was about 1.9 cm, the water volume was about 1000 ml, the application amount was 0.02 ml of surface film, and the styrofoam weight was about 0.1 grams.

What is claimed:

1. A method of controlling the population of mosquitoes comprising:
    c) applying a surface-active composition to an aquatic environment to form a film over water within that environment, and
    d) allowing the film to remain at or near the air-surface interface of an aquatic environment for sufficient time to contact at least some surface-active life cycle stage of mosquitoes within that environment, wherein said composition comprises at least 10% by weight of organic material within said composition of at least one $C_6$ to $C_{11}$ alcohol alkoxylate, wherein the average carbon content of alcohols in the composition is less than $C_{11}$, wherein said composition is free of any effective amount of insecticide of the class of central nervous system insecticide, endocrine insecticide, stomach insecticide, or contact insecticide in addition to the at least 10% by weight of organic material.

2. A method according to claim 1 wherein said alkoxylates comprise ethoxylates and/or propoxylates.

3. The method of claim 1 wherein said alkoxylates have an average of one (1) to five (5) moles of ethylene and/or propylene oxide per mole of alcohol in the alkoxylate.

4. The method of claim 1 wherein said composition comprises at least 50% by weight of organic materials of said at least one $C_6$ to $C_{11}$ alcohol alkoxylate.

5. The method of claim 1 wherein said composition is applied by direct application of a solid material carrying absorbed or adsorbed composition to a dry environment where mosquito eggs are present.

6. The method of claim 1 wherein said composition is applied to the environment by application of a solid material carrying absorbed or adsorbed composition to the environment.

7. The method of claim 1 wherein said alkoxylate is selected from the group consisting of:

a mixture of $C_9$–$C_{11}$ alcohol ethoxylates with average of 2–5 moles of ethylene oxide per mole of alcohol, $C_{11}$ alcohol ethoxylates with 3 to 5 moles of ethylene oxide per mole of alcohol, and $C_6$–$C_{10}$ and $C_8$–$C_{10}$ alcohol ethoxylate mixtures containing between 2 and 4 moles of ethylene oxide per mole of alcohol.

8. The method of claim 1 wherein said composition consists essentially of $C_6$ to $C_{11}$ alcohol alkoxylates.

9. The method of claim 1 wherein said composition consists essentially of $C_6$ to $C_{10}$ alcohol alkoxylates.

10. The method of claim 1 wherein said composition consists essentially of at least 90% by weight of organic material within said composition of at least one $C_6$ to $C_{11}$ alcohol alkoxylate, wherein the average carbon content of alcohols in the composition is less than $C_{11}$.

11. A method of controlling the breeding of mosquitoes which have an aquatic phase in their life cycle, comprising applying organic material to a water environment an insecticide composition comprising an effective insecticidal amount of a first component which forms an insoluble or partially insoluble monomolecular layer or multimolecular layer or an insoluble or partially soluble foam layer on the surface of the water, each of which layers effectively kills mosquitoes at certain stages in their life cycle, said first component comprising at least 10% by weight of the organic material within said composition of at least one $C_6$ to $C_{11}$ alcohol alkoxylate, wherein the average carbon content in alcohol groups in the organic material is less than $C_{11}$, wherein said composition is free of any effective amount of insecticide of the class of central nervous system insecticide, endocrine insecticide, stomach insecticide, or contact insecticide in addition to the at least 10% by weight of organic material.

* * * * *